US007276595B2

(12) United States Patent
Ip et al.

(10) Patent No.: US 7,276,595 B2
(45) Date of Patent: Oct. 2, 2007

(54) DNA SEQUENCE ENCODING A RETINOIC ACID REGULATED PROTEIN

(75) Inventors: Nancy Y. Ip, Hong Kong (HK); William M. W. Cheung, Sunshine (HK)

(73) Assignee: Hong Kong University of Science & Technology Inc., Clear Water Bay, Kowloon (HK)

( * ) Notice: Subject to any disclaimer, the term of this patent is extended or adjusted under 35 U.S.C. 154(b) by 602 days.

(21) Appl. No.: 10/726,160

(22) Filed: Dec. 2, 2003

(65) Prior Publication Data

US 2005/0037372 A1    Feb. 17, 2005

Related U.S. Application Data

(60) Continuation-in-part of application No. 10/409,511, filed on Apr. 8, 2003, now abandoned, which is a division of application No. 09/354,359, filed on Jul. 14, 1999, now abandoned.

(51) Int. Cl.
| | |
|---|---|
| *C07H 21/00* | (2006.01) |
| *C07H 5/00* | (2006.01) |
| *C07H 19/00* | (2006.01) |
| *C08B 37/00* | (2006.01) |
| *C12N 15/00* | (2006.01) |
| *C12N 15/09* | (2006.01) |
| *C12N 15/63* | (2006.01) |
| *A61K 38/00* | (2006.01) |
| *C07K 14/00* | (2006.01) |
| *C07K 16/00* | (2006.01) |
| *C07K 17/00* | (2006.01) |
| *C07K 2/00* | (2006.01) |
| *C07K 4/00* | (2006.01) |
| *C07K 5/00* | (2006.01) |

(52) U.S. Cl. .................. 536/23.5; 536/18.7; 536/22.1; 536/23.1; 536/24.1; 536/24.2; 435/320.1

(58) Field of Classification Search ............. 435/320.1; 536/24.2, 187, 221, 23.5, 23.1, 24.1
See application file for complete search history.

(56) References Cited

U.S. PATENT DOCUMENTS 5,856,129 A    1/1999    Hillman et al.

OTHER PUBLICATIONS

Reiners et al. Molecular basis of human Usher syndrome: Deciphering the meshes of the Usher protein network provides insights into the pathomechanisms of the Usher disease. Experimental Eye Research 83: 97-119, 2006).*
Lewin, Benjamin. Genes IV, Oxford University Press, p. 810, Cambridge, 1990.
Nucleic acid database, Accession #AI023761, 1998.
Nucleic acid database, Accession #AA913841, 1998.
Nucleic acid database, Accession #AA846697, 1998.
Article—*Rising Incidence of Hepatocellular Carcinoma in the United States*, Hashem B. El-Serag and Andrew C. Mason, The New England Journal of Medicine, vol. 340, No. 10, Mar. 11, 1999, pp. 745-750.
Article—*Utilization of Nuclear Matrix Proteins for Cancer Diagnosis*, Susan K. Keesee, Joseph V. Briggman, Gregory Thill, and Ying-Jye Wu, Critical Reviews in Eukaryotic Gene Expression, vol. 6, 1996, pp. 189-214.
Article—*Evaluation of the Clinical Value of Urinary NMP22 as a Marker in the Screening and Surveillance of Transitional Cell Carcinoma of the Urinary Bladder*, R. Chahal, A. Darshane, A.J. Browning, and S.K. Sundaram, European Urology, vol. 40, Mar. 14, 2001, pp. 415-421.
Article—*Nuclear matrix proteins as biomarkers for breast cancer*, Diana Lüftner and Kurt Possinger, Expert. Rev. Mol. Diagn., vol. 2, 2002, pp. 23-31.
Article—*Prognostic value of nuclear survivin expression in oesophageal squamous cell carcinoma*, P. Grabowski, T. Kühnel, F. Mühr-Wilkensoff, B. Heine, H. Stein, M. Höpfner, C.T. Germer, and H. Scherübl, British Journal of Cancer, vol. 88, 2003, pp. 115-119.
Article—*T c-myc oncogene: use of a biological prognostic marker as a potential target for gene therapy in melanoma*, J. S. Chana, R. Grover, P. Tulley, H. Lohrer, R. Sanders, A. O. Grobbelaar, and G. D. Wilson, British Journal of Plastic Surgery, vol. 55, 2002, pp. 623-627.
Estimated New Cancer Cases and Deaths by Sex, US, 2003, from Cancer Facts & Figures 2003, American Cancer Society, Inc., Surveillance Research, 2 pages.
Percentage Distribution of Microscopically Verified Cases by Histological Type Liver (ICD-9 155)—Both Sexes from Cancer Incidence in Five Continents, vol. VII, D.M. Parkin, S.L. Whelan, J. Ferlay, L. Raymond, and J. Young, IARC Scientific Publications No. 143, 1997, pp. 1072-1074.
Article—"The potential role for prolactin-inducible protein (PIP) as a marker of human breast cancer micrometastasis", Authors—JW Clark et al., British Journal of Cancer (1999) 81(6), 1002-1008.
Article—"Expression of MAGE-1 -3 genes and gene products in human hepatocellular carcinoma", Authors—K Kariyama et al., British Journal of Cancer (1999) 81(6), 1080-1087.
Article—"Increased Expression of COX-2 in Nontumor Liver Tissue Is Associated with Shorter Disease-free Survival in Patients with Hepatocellular Carcinoma", Authors—M Kondo et al., Clinical Cancer Research 4005, vol. 5,4005-4012, Dec. 1999.

* cited by examiner

*Primary Examiner*—Alana M. Harris
(74) *Attorney, Agent, or Firm*—Dority & Manning, P.A.

(57) ABSTRACT

The present invention concerns a novel retinoic acid regulated gene whose expression product displays useful morphogenic/mitogenic properties. The present invention further concerns an isolated nucleic acid of SEQ ID NO:1 encoding a retinoic acid regulated expression product having an amino acid sequence of SEQ ID NO:2.

4 Claims, 8 Drawing Sheets

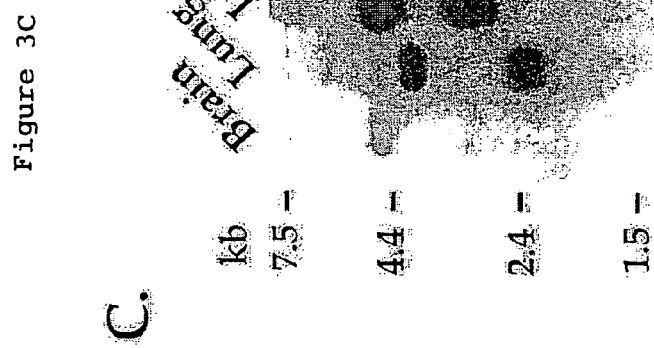
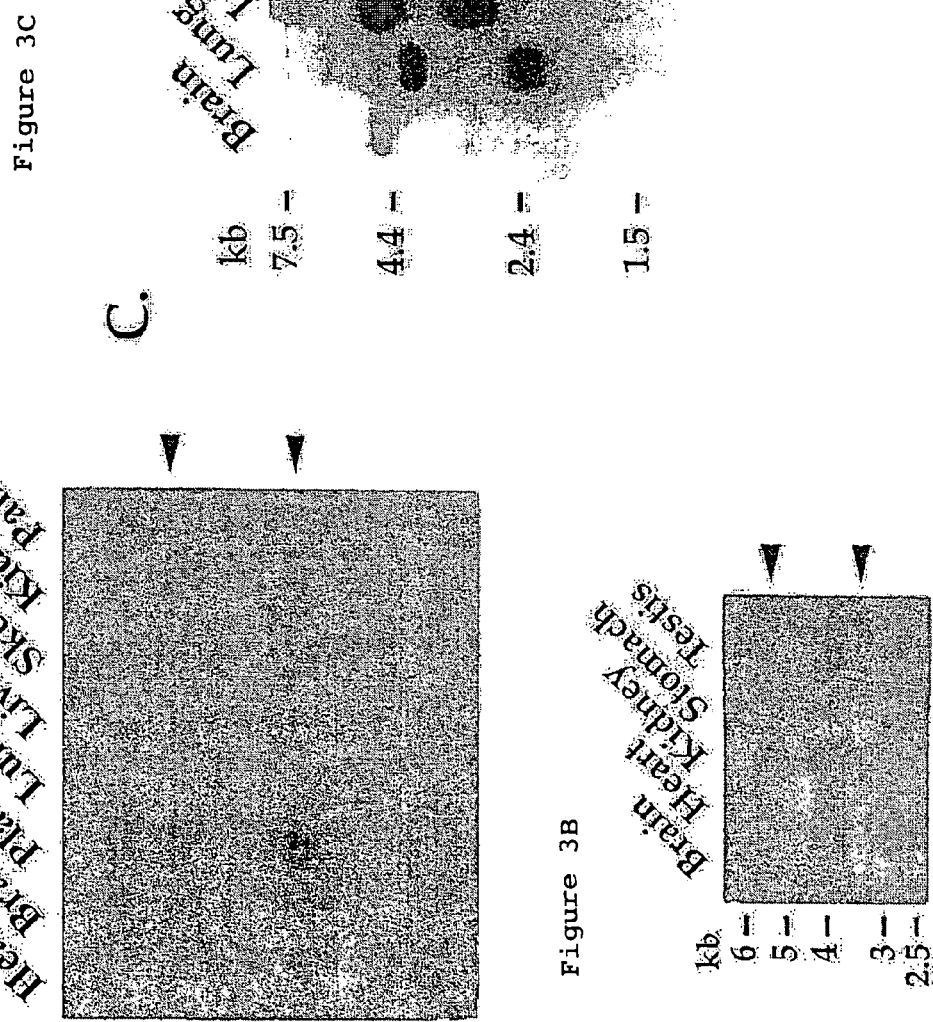
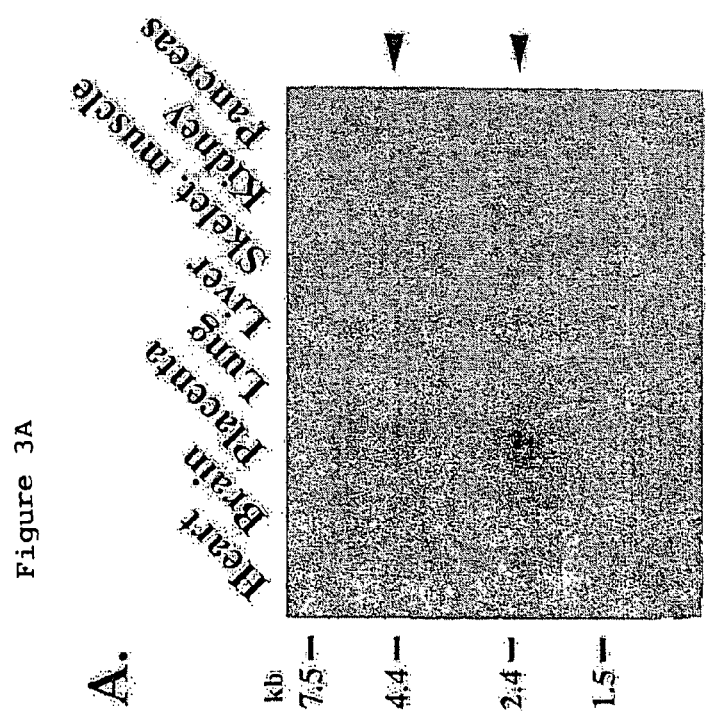
Figure 3A
Figure 3B
Figure 3C

US 7,276,595 B2

DNA SEQUENCE ENCODING A RETINOIC ACID REGULATED PROTEIN

CROSS-REFERENCE TO RELATED APPLICATIONS

The present application is a continuation-in-part application of U.S. application Ser. No. 10/409,511, filed on Apr. 8, 2003, now abandoned which is incorporated herein in its entirety by reference thereto for all purposes. Application Ser. No. 10/409,511 is a divisional application of U.S. application Ser. No. 09/354,359, filed on Jul. 14, 1999, now abandoned.

FIELD OF THE INVENTION

The present invention is concerned with a novel retinoic acid (RA) regulated gene whose expression product displays useful morphogenic/mitogenic properties. In particular, the present invention is concerned with uses of the expression product. For example, the expression product may be used generally as a tumor biomarker or as an indicator for Hepatocellular carcinoma (HCC). The marker or indicator can also serve as a screening and supporting tool for the diagnosis of tumor such as HCC, and is also useful for monitoring treatment and tumor progression.

BACKGROUND OF THE INVENTION

Retinoic acid induces the differentiation of many cell types, such as epithelial cells, mesenchyme cells, teratocarcinoma cells, leukaemia cells and immortalized cell lines such as embryonal carcinoma cells and neuroblastoma cells. RA is a morphogen which specifies axial patterning during embryonic development and which affects neurogenesis, and has been used as an effective therapeutic agent for the treatment of acute promyelocytic leukaemia.

The exact mode of action of retinoic acid is currently unknown, although it is known to be mediated by the nuclear retinoic acid receptors (RARs) (Chambon, P., 1996, FASEB J., 10: 940-959), and it is hypothesised that the diverse effects of RA result from the differential regulation of proteins such as transcription factors, enzymes and growth factor receptors.

Cheung, W. M. W. et al. (1997, J. Neurochem., 68: 1882-1888) have used RNA fingerprinting by arbitrarily primed PCR to identify a large number of genes that are differentially regulated during RA-induced neuronal differentiation. The present inventors have succeeded in isolating, purifying and cloning a novel gene which is down-regulated during RA-induced neuronal differentiation and whose resultant protein product possesses morphogenic/mitogenic properties.

SUMMARY OF THE INVENTION

According to a first aspect of the present invention, there is provided an isolated nucleic acid of SEQ ID NO:1 encoding a retinoic acid regulated expression product having the amino sequence depicted in SEQ ID NO:2.

According to an additional aspect of the present invention, there is provided an expression product of an isolated nucleic acid of SEQ ID NO:1. Suitably, the nucleic acid or the expression product thereof may be used as a screening or supporting tool for the diagnosis of Hepatocellular carcinomas (HCC). The expression product may also be adapted for monitoring treatment or progression of Hepatocellular carcinomas (HCC).

According to another aspect of the present invention, there is provided an antibody comprising the amino acid sequence depicted in SEQ ID NO:4 that binds specifically to a retinoic acid regulated nuclear matrix protein (RAMP) having an amino acid sequence depicted in SEQ ID NO:2.

The present invention is also directed to providing an antibody comprising the amino acid sequence depicted in SEQ ID NO:5 that binds specifically to a retinoic acid regulated nuclear matrix protein (RAMP) having the amino acid sequence depicted in SEQ ID NO:2.

According to an additional aspect of the present invention, there is provided a recombinant DNA construct comprising operatively linked in sequence in the 5' to 3' direction: (i) a promoter region that directs the transcription of a gene; (ii) a DNA coding sequence encoding an RNA sequence encoding an expression product having the sequence depicted in SEQ ID NO:2; and (iii) a 3' non-translated region. In particular, the DNA coding sequence may comprise the sequence of SEQ ID NO:1. In other embodiments of the present invention, there is provided a cell transformed or transfected with the recombinant DNA construct described above.

According to another aspect of the present invention, there is provided an isolated nucleic acid comprising a nucleotide sequence encoding the amino acid sequence depicted in SEQ ID NO:2.

In other embodiments of the present invention, there is provided a method for screening and determining the prognosis of a patient having Hepatocellular cancer (HCC), the method comprising the steps of: (i) obtaining biological samples from the patient; (ii) isolating proteins from the biological samples; (iii) contacting the proteins with a specific antibody that binds specifically to a retinoic acid regulated nuclear matrix protein (RAMP) comprising the amino acid sequence depicted in SEQ ID NO:2; and (iv) detecting the presence of an expression product of SEQ ID NO:1 having the amino acid sequence depicted in SEQ ID NO:2. The biological samples may comprise liver tissues, while the antibody may be a polypeptide.

According to an additional aspect of the present invention, there is provided a gene having the sequence depicted in SEQ ID NO:1. Also provided is an expression product encoded by the gene of the present invention, and in particular an expression product of the gene having the sequence depicted in SEQ ID NO:2. The present invention also extends to allelic mutants of the gene and gene expression product, and also to modified forms of the nucleic acid sequence which encode the expression product. For example, modifications may be made to the nucleic acid sequence such that it has a different sequence yet still codes for the same amino acid sequence.

Experiments (described in more detail below) show that the expression product is important in maintaining the stem cell identity of the progenitor cells, as well as in the early differentiation of the progenitor cells. It is also important in embryogenesis and also appears to participate in the functioning of adult tissues, particularly brain, lung, liver and kidney. Expression of the gene product in lymphoid tissues shows a restrictive profile in the T-cell lineage of the immune system, particularly in the thymus and the bone marrow.

The gene of the present invention may also have applications in the treatment of Ushers disease, particularly type II Ushers disease, and thus the present invention extends to the use of the gene and its expression product in the manufacture of medicaments for treating Ushers disease, together with methods of treatment of Ushers disease.

Thus, the gene of the present invention is useful both in treating and preventing diseases associated with its expression, with morphogeny and mitogeny, and with Ushers disease, particularly type II Ushers disease.

The expression product according to the present invention may be a mitogen and/or a morphogen. Further, the expression product of the present invention may be usefully provided in the form of a recombinant construct, allowing its expression by chosen organisms under chosen conditions.

According to another aspect of the present invention, there is also provided a DNA molecule, which may be in recombinant or isolated form, comprising a sequence encoding an expression product according to the present invention.

The coding sequence may be operatively linked to an expression control sequence sufficient to drive expression. Recombinant DNA in accordance with the invention may be in the form of a vector, for example a plasmid, cosmid or phage. A vector may include at least one selectable marker to enable selection of cells transfected (or transformed) with the vector. Such a marker or markers may enable selection of cells harbouring vectors incorporating heterologous DNA. The vector may contain appropriate start and stop signals. The vector may be an expression vector having regulatory sequences to drive expression. Vectors not having regulatory sequences may be used as cloning vectors (as may expression vectors).

Cloning vectors can be introduced into suitable hosts (for example E. coli) which facilitate their manipulation. According to another aspect of the invention, there is therefore provided a host cell transfected or transformed with DNA according to the present invention. Such host cells may be prokaryotic or eukaryotic. Expression hosts may be stably transformed. Unstable and cell-free expression systems may of course also be used.

Expression hosts may contain other exogenous DNA to facilitate the expression, assembly, secretion and other aspects of the biosynthesis of molecules of the invention.

The present invention may be used with synthetic DNA sequences, cDNAs, full genomic sequences and "minigenes", i.e. partial genomic sequences containing some, but not all, of the introns present in the full-length gene.

DNA according to the present invention may be prepared by any convenient method involving coupling together successive nucleotides, and/or ligating oligo- and/or polynucleotides, including in vitro processes, as well as by the more usual recombinant DNA technology.

Also provided according to another aspect of the present invention is a recombinant DNA construct comprising operatively linked in sequence in the 5' to 3' direction:
 a) a promoter region that directs the transcription of a gene;
 b) a DNA coding sequence encoding an RNA sequence encoding an expression product of the present invention; and
 c) a 3' non-translated region.

The DNA coding sequence may have the sequence of SEQ ID NO:1.

Also provided is a cell transformed or transfected with a recombinant DNA construct of the present invention.

Also provided is a method of treating or preventing diseases associated with the expression of a gene of the present invention, comprising administering to a patient an expression product of the present invention.

As well as simply expressing the gene or administering the gene product in order to effect treatment of a patient, it may also be desirable to inhibit (i.e. antagonise) the gene product. This can be achieved in a multitude of ways, as will be readily apparent to one skilled in the art. In particular, U.S. Pat. No. 5,856,129 to Hillman, et al. and the references cited therein provide information regarding how to produce and identify antagonists, inhibitors and potentiators of gene products. U.S. Pat. No. 5,856,129 to Hillman, et al. is incorporated herein in its entirety by reference thereto for all purposes. In particular, the following additional teachings may be used: Harlow, E. and Lane, D., "Using Antibodies: A Laboratory Manual", Cold Spring Harbour Laboratory Press, New York, 1998; Sambrook, J., Frisch, E. F., and Maniatis, T., "Molecular Cloning. A Laboratory Manual", Cold Spring Harbour Laboratory, Cold Spring Harbour Press, New York, 1989; Ausubel, F. M. et al., 1989, Current Protocols in Molecular Biology, John Wiley & Sons, New York, N.Y.; Gee, J. E. et al., 1994, In: Huber, B. E. and Carr, B. I. Molecular and Immunologic Approaches, Futura Publishing Co., Mt. Kisco, N.Y.

The invention will be further apparent from the following description with reference to the figures, which shows by way of example only the cloning and study of the gene of the present invention.

BRIEF DESCRIPTION OF THE DRAWINGS

FIG. 3 shows the expression profile of 8.31 in human tissues. Multiple Tissue Northern blots (Clontech) were hybridized using full-length 8.31 cDNA as probe. Results of the hybridization using adult tissues (FIGS. 3A and 3B) and fetal tissues (FIG. 3C) are shown. RNA size markers are indicated on the left;

EXAMPLES

Example I

Hepatocellular carcinoma (HCC) is the most common primary cancer of the liver. (Parkin D M, Whelan S L, Ferlay J, et al., eds.: Cancer Incidence in Five Continents: Volume VII. Lyon, France: IARC Scientific Publications, pp. 1072-1074, 1997). In the United States, it is estimated that there will be 17,300 new cases in liver and intra hepatic bile duct cancer and 14,400 deaths in 2003 (American Cancer Society: Cancer Facts and FIGS. 2003. Atlanta, Ga.: American Cancer Society, p. 4, 2003). Over the past two decades, the number of cases of HCC in the United States increased substantially and the age-specific incidence of this cancer has progressively shifted towards younger people with age between 40 to 60 years old (EL-Serag H B, Mason A C. Rising Incidence of Hepatocellular Carcinoma in the United States. The New England Journal of Medicine 340 (10): 745-750, 1999).

Alterations in nuclear morphology are hallmarks of cancer and are believed to be associated with changes in nuclear matrix composition. Nuclear matrix provides structural support for the nucleus and plays a dynamic role in the spatial organization of the genome and in the control of DNA replication and transcription. The recovery of increased amount of specific nuclear matrix proteins (NMP) in several different cancers has led to the further study of some of these proteins as a new class of tumor markers (Keesee S K, Briggman J V, Thill G, Wu Y J: Utilization of Nuclear Matrix Proteins for Cancer Diagnosis. Critical Reviews in Eukaryotic Gene Expression 6 (2&3): 189-214, 1996). Recently, specific nuclear matrix proteins have been isolated and were demonstrated to have prognostic value: NMP22 as a marker for transitional cell carcinoma of urinary bladder (Chahal R, Darshane A, Browning A J, Sundaram S K: Evaluation of the clinical value of urinary NMP22 as a marker in the screening and surveillance of transitional cell carcinoma of the urinary bladder. Eur Urol. 40: 415-20, 2001); NMP66 as a marker for breast cancer (Luftner D, Possinger K: Nuclear matrix proteins as biomarkers for breast cancer. Expert Rev Mol Diagn 2(1): 23-31, 2002); NMP survivin expression in oesophageal squamous cell carcinoma (Grabowski P, Kuhnel T, Muhr-Wilkenshoff F, Heine B, Stein H, Hopfner M, Germer C T, Scherubl H: Prognostic value of nuclear survivin expression in oesophageal squamous cell carcinoma. Br J Cancer 88: 115-9, 2003); and c-myc as a marker for melanoma (Chana J S, Grover R, Tulley P, Lohrer H, Sanders R, Grobbelaar A O, Wilson G D: The c-myc oncogene: use of a biological prognostic marker as a potential target for gene therapy in melanoma. Br J Plast Surg 55: 623-7, 2002).

Figure 8:
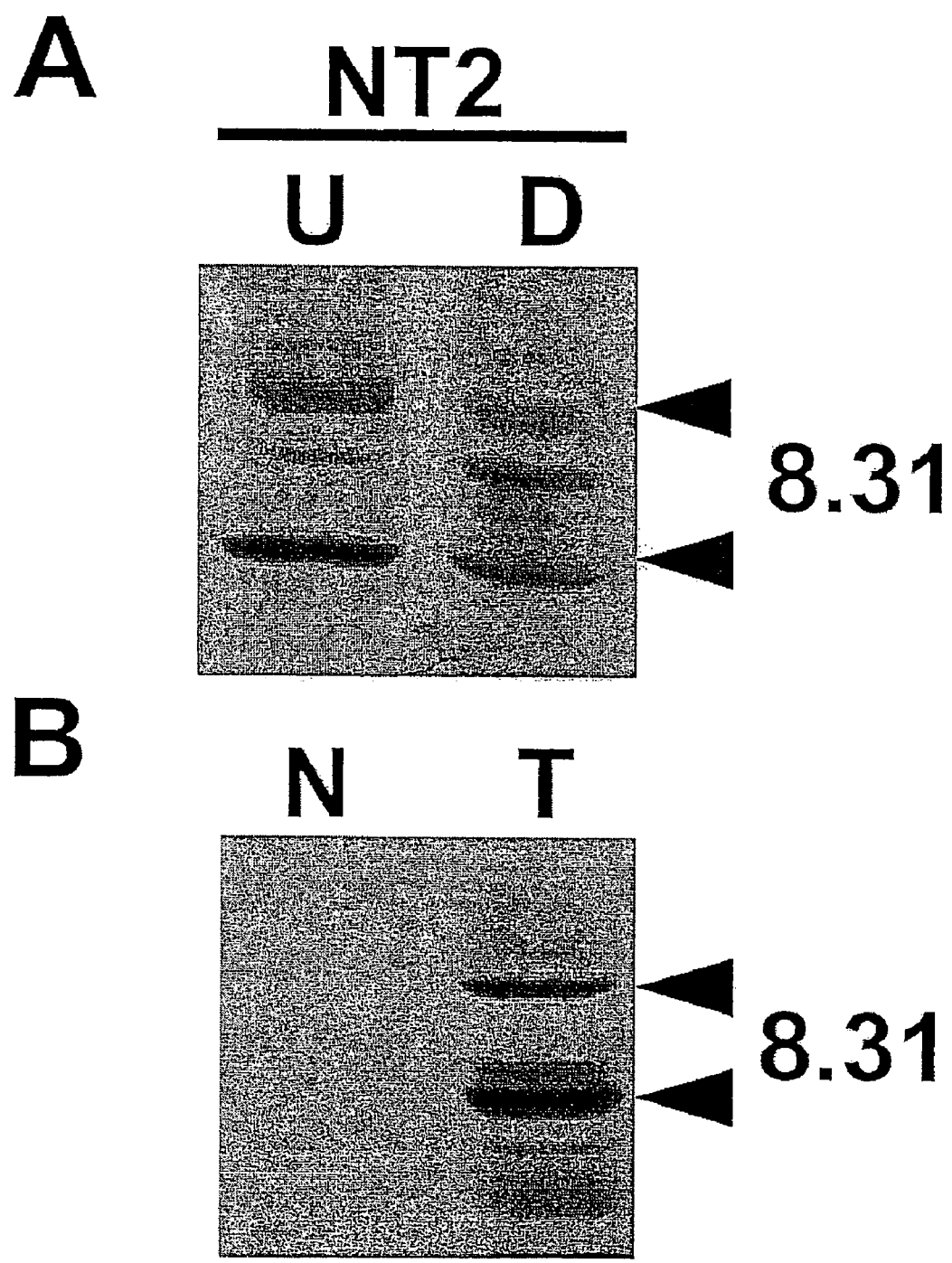
FIG. 8 shows the expression of a gene product encoding for RAMP in the tumor of a HCC patient. The gene products encoding for RAMP from protein extracts of a HCC patient is shown as "N" for normal tissues adjacent to the tumor (FIG. 8B); "T" for tumor samples (FIG. 8B); "U" for undifferentiated NT2 cells used to normalize the expression of RAMP between blots (FIG. 8A) and "D" for differentiated NT2 cells by retinoic acid (FIG. 8A).

The present invention identified a novel gene comprising an isolated nucleic acid sequence according to SEQ ID NO:1, the expression product of which, a novel retinoic acid regulated nuclear matrix protein (RAMP), is detected in over 70% of patient samples at the early stages of HCC while the normal liver tissue adjacent to the tumor tissue has showed a very low or undetectable expression of RAMP. Immunoreactive bands detected by the antibody recognizing RAMP were at about 80 kDa in tumor samples (FIG. 8). Intensity of the RAMP immunoreactive protein bands was quantitated by densitometry. In tumors, an overexpression of RAMP was determined when there was an at least twofold increase in the intensities of the immunobands compared to adjacent normal tissues. Specifically, 22 out of 28 carcinomas revealed an overexpression of the RAMP. Of these RAMP overexpressing tumors, 16 samples exhibited an additional lower molecular weight RAMP band, migrating to about 60 kDa (FIG. 8). In some of the tumors the lower molecular weight isoforms were even more abundant than the higher molecular weight protein of RAMP (FIG. 8).

FIG. 8 is concerned with the expression of a gene product encoding for RAMP in the tumor of a HCC patient. Examples of a representative Western blot analysis was used to show the expression of gene products encoding for RAMP from protein extracts of a HCC patient (N, normal adjacent tissues; T, tumor samples). Protein (20 µg) was loaded to each lane. The expression of gene product for RAMP in undifferentiated NT2 cells (U) was used to normalize the expression of RAMP between blots.

Materials and Methods:

Hepatocellular carcinomas (n=28) and matched adjacent normal liver tissues (n=28) were obtained. The tissues were stored at −80° C. before processing. The proteins were extracted from tumor and adjacent normal tissues of different individuals. Protein concentration of the lysates was determined using Bio-Rad Protein Assay kit (Bio-Rad). The protein was then resuspended in sample buffer. The composition of the sample buffer was 0.125 M Tris-HCl buffer (pH 6.8), 4% SDS, 10% β-mercaptoethanol, 20% glycerol and 0.002% bromophenol blue. The mixture was boiled for 3 min and then the supernatant was loaded in the SDS-polyacrylamide gel.

Equal amount of protein was separated on SDS-PAGE gels. SDS-PAGE was carried out using a 7.5% acrylamide resolver gel and 4% stacker gel according to Laemmli et al. (1970). The stacker and resolver gels were prepared according to the protocol supplied with the electrophoresis apparatus, Mini-Protein II (Hoefer, Amersham Biosciences). The samples were loaded into the wells of a 1.0 mm thick gel and electrophoresed with 20 mA through the stacker gel and 30 mA after entering the resolver gel for 3 hr in 25 mM Tris-HCl and 192 mM glycine (pH 8.3), containing 0.1% SDS. Prestained molecular weight markers and protein sample of undifferentiated NT2 cells were run alongside the samples.

The proteins on the polyacrylamide gel were transferred onto a nitrocellulose membrane in 1× transfer buffer using a Trans-Blot electrophoretic transfer cell (Bio-Rad, CA, USA) at 100 V for 1 hr at 4° C. The membrane was washed with Tris-buffered saline with 0.1% Tween-20 (TBS-T). The membrane was blocked with 5% non-fat dry milk in TBS-T for 1 hr at room temperature. The membrane was then incubated with RAMP antibody (1:500) in 1×TBS-T with 5% BSA at 4° C. overnight, followed with horseradish peroxidase conjugated secondary antibodies in TBS-Tween with 5% nonfat milk at room temperature for 1 hr. The immunoreactive proteins were detected using Pico detection system (Pierce, Rockford, USA) according to the supplier's instruction.

Example II

The gene of the present invention (also referred to as clone 8.31) was cloned and expressed, its in vitro transcription and translation assayed and its chromosomal location determined. The expression profile of 8.31 in a range of cell types and under a range of conditions has allowed a role for it to be determined.

Materials and Methods:

Experimental methods referred to and used are standard laboratory techniques. Where specific methods are not described or referenced, full descriptions and protocols are well known in the art and available in laboratory manuals such as Harlow, E. and Lane, D., "Using Antibodies: A Laboratory Manual", Cold Spring Harbor Laboratory Press, New York, 1998; Sambrook, J., Frisch, E. F., and Maniatis, T., "Molecular Cloning. A Laboratory Manual", Cold Spring Harbor Laboratory, Cold Spring Harbor Press, New York, 1989; PCR (Volume 1): A practical approach. Eds. M. J. McPherson, P. Quirke and G. R. Taylor. Oxford University Press, 1991; and Torres, R. M. and Kuhn, R., "Laboratory Protocols for Conditional Gene Therapy", Oxford University Press, 1997, ISBN 019963677-X.

Cloning of Full Length cDNA of 8.31:

Full length cDNA of 8.31 was obtained by screening an expression cDNA library prepared from undifferentiated NT2 cells (STRATAGENE) using the partial 8.31 cDNA fragment (SEQ ID NO:3) as probe. Radioactive cDNA probes were prepared using the Megaprime DNA labelling system (AMERSHAM). Single phages were obtained and transformed into XLOLR bacterial cells (STRATAGENE) and the cDNA fragment cloned into pBK-CMV mammalian expression vector by in vivo excision.

Cell Culture:

NT2 cells were cultured as previously described (Cheung et al., 1996, NeuroReport, 6: 1204-1208). Cells were maintained in Opti-MEM I reduced-serum medium (GIBCO) supplemented with 5% fetal bovine serum (FBS, GIBCO). NT2 cells were differentiated with 5 µM all-trans RA (SIGMA) in Dulbecco's modified Eagle's medium (DMEM; high glucose formulation) supplemented with 10% FBS. Leukaemia cell lines were cultured as previously described (Xie et al., 1997, NeuroReport, 8: 1067-1070).

8.31 cDNA Probe:

The partial cDNA sequence of 8.31 was obtained using RNA fingerprinting by arbitrarily primed PCR (RAP-PCR, Welsh, J. et al., 1992, Nucleic Acids Res., 20: 4965-4970). Total RNA was obtained from NT2 cells treated for various durations with all-trans RA (10 M). The differentially-regulated cDNA fragments were cloned into pCRscript SK+ for DNA sequencing. The cDNA probe (SEQ ID NO:3) was then used to screen an undifferentiated human NT2 cell cDNA library for the full length 8.31 cDNA.

RNA Preparation, RT-PCR and Northern Blot Analysis:

Total RNA was prepared using Trizol reagent (GIBCO) or as previously described (Xie et al., 1997, NeuroReport, 8: 1067-1070). Equal amounts of total RNA from different cell lines were used for Northern blot analysis, while 2 µg total RNA was used for reverse transcription using Superscript II reverse transcritptase (GIBCO). One tenth of the reaction was amplified using Taq DNA polymerase (GIBCO). Gene expression was confirmed by using different numbers of PCR cycles and hybridization using 8.31 specific cDNA probes.

Coupled In Vitro-transcription and Translation:

Two micrograms of plasmids were used for each coupled in vitro transcription/translation reaction using the TNT coupled reticulocyte lysate system (PROMEGA).

Chromosomal Localization of 8.31 by FISH (Fluorescent In Situ Hybridisation):

Genomic DNA encoding 8.31 was labeled with digoxigenin (DIG) dUTP by nick translation and was hybridized to normal metaphase chromosomes derived from PHA phytohemaglutinin stimulated peripheral blood lymphocytes. After incubation with fluorescein-conjugated anti-DIG antibodies, the cells were counterstained with DAPI (4,6-diamidino-2-phenylindole), a fluorescent DNA groove-binding probe.

Figure 1:
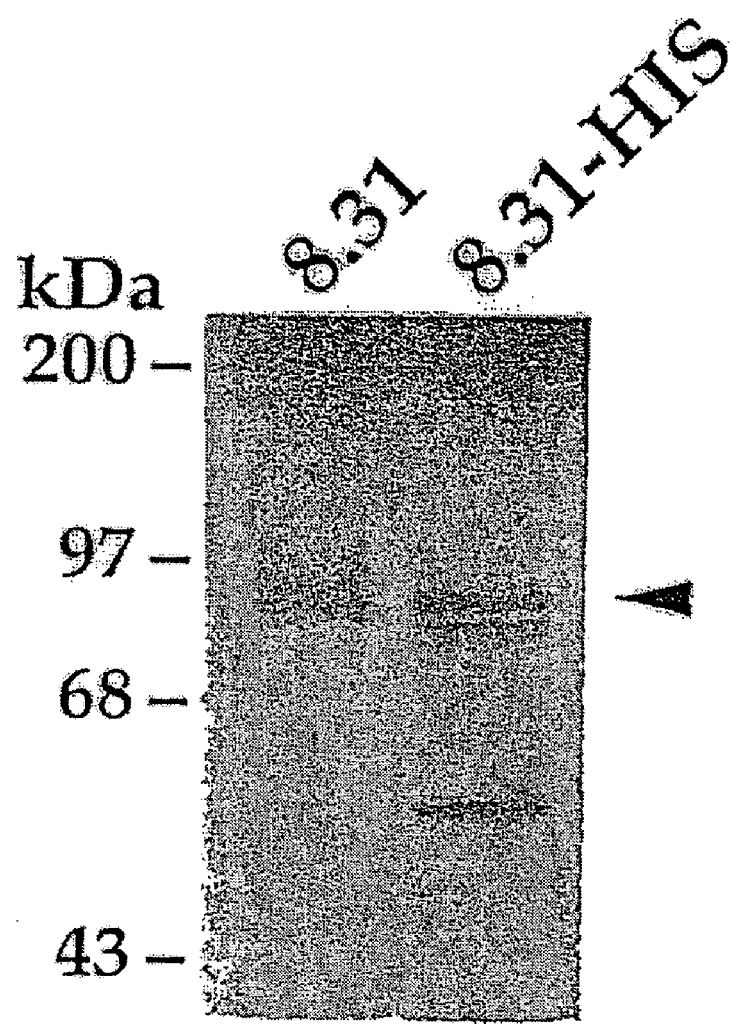
FIG. 1 shows coupled in vitro transcription and translation using rabbit reticulocyte extract, demonstrating that full length 8.31 cDNA encoded a ~80 kDa protein. Histidine (His)-tagged 8.31 protein was constructed by cloning 6 His to the C-terminus of 8.31. Coupled in vitro transcription and translation was performed in the absence of radioactive label. The translated proteins were separated by SDS PAGE, transferred to nitrocellulose membrane and blotted with monoclonal antibody against the 6×His tail.

Results:

Cloning of Full Length Coding Sequence of 8.31:

The cDNA encoding the full length 8.31 was obtained from a cDNA library prepared from undifferentiated NT2 cells using hybridization screening. Double stranded sequencing by T7 DNA polymerase revealed that the cDNA (~2831 bp) is novel in its gene identity (FIG. 1). The coding sequence can be translated into a protein of 730 amino acid residues. Coupled in vitro transcription and translation was performed to demonstrate that the cloned cDNA can be translated into a protein with molecular weight of ~80 kDa (FIG. 1).

Figure 2:
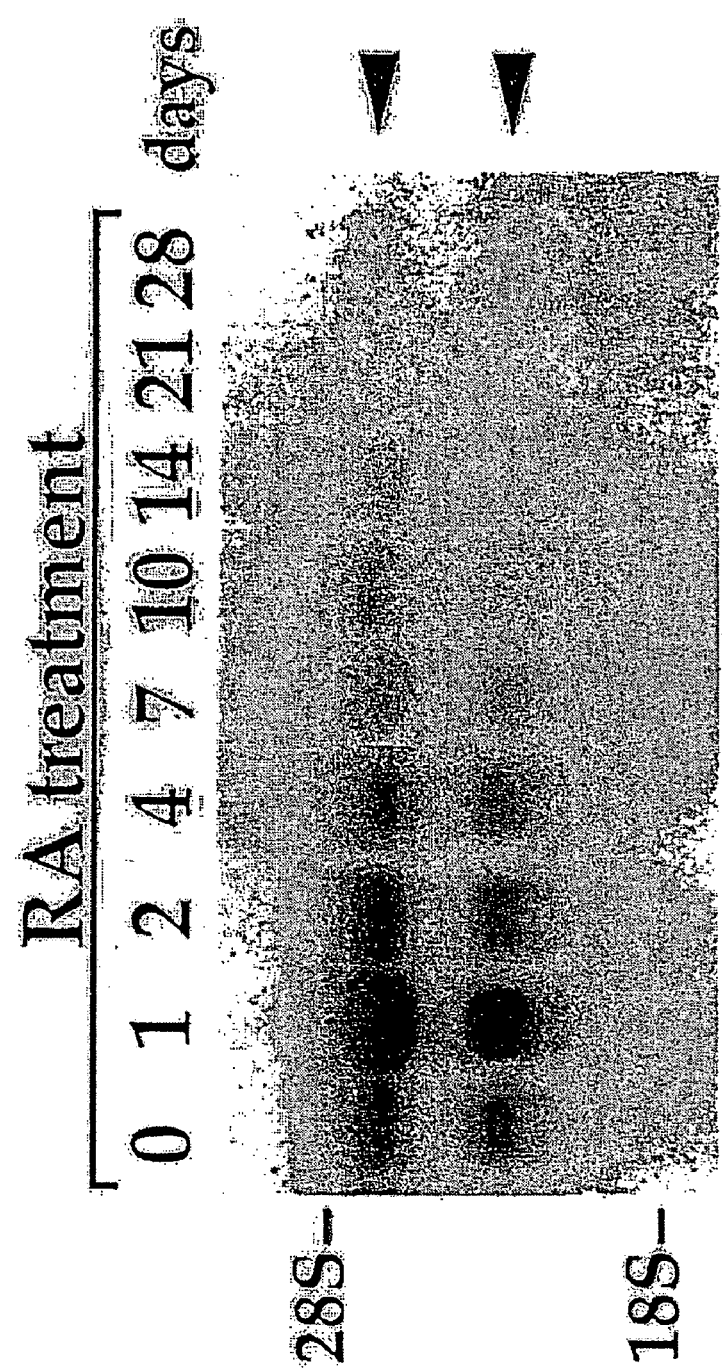
FIG. 2 shows Northern blot analysis of 8.31 expression in RA-treated NT2 cells. Total RNA (10 µg) prepared from NT2 cells treated with all-trans RA for 0 to 28 days, separated by denaturing gel electrophoresis, and transferred to nylon membrane. Hybridization was performed using the full-length 8.31 cDNA as probe. Ribosomal RNA bands are as shown on the left.

Transcript Expression of 8.31:

The full length 8.31 was then used as a probe to examine its expression when the NT2 cells were treated with RA for 0 to 28 days (FIG. 2). Two transcripts were obtained (~4.5 kb and ~3.5 kb). The expression of 8.31 was slightly induced after 1 day of RA treatment. At day 2, the expression decreased to its basal level and then continue to decrease along the course of RA treatment. Its expression was almost halted at day 28.

To obtain clues on the potential functions of 8.31, we examined the expression profile of 8.31 in both adult and fetal human tissues. Among the adult tissues examined, which include heart, brain, placenta, lung, liver, skeletal muscle, kidney, pancreas, stomach, and testis, prominent expression of 8.31 was observes in placenta and testis. Skeletal muscles expressed low levels of 8.31 (FIG. 3, panels A and B).

The expression of 8.31 was observed in all the human fetal tissues examined, which included brain, lung, liver and kidney. An extra transcript (~5.5 kb) was observed in all fetal tissues and a small transcript (~2.4 kb) was observed only in the messenger RNA prepared from the fetal lung (FIG. 3, panel C). The high expression of 8.31 in the fetal tissues examined was not observed in the corresponding adult tissues.

Figure 4:
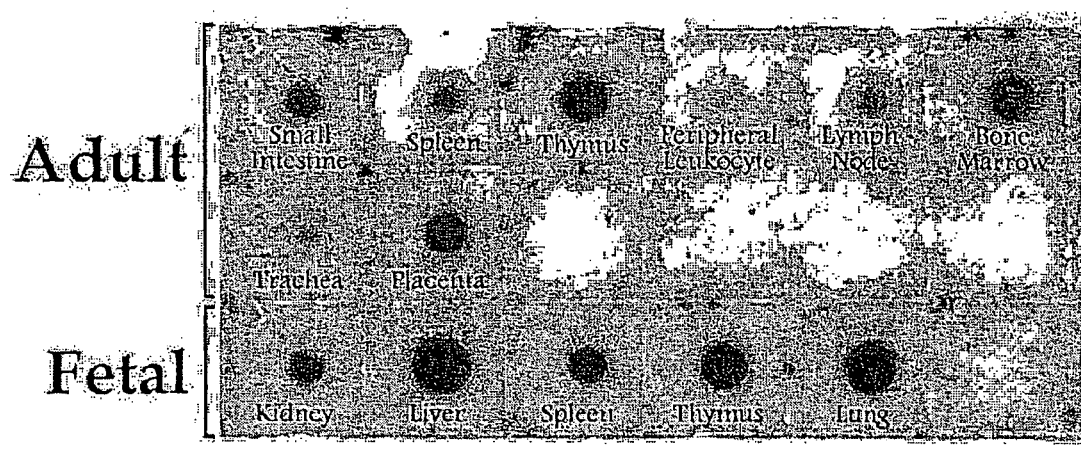
FIG. 4 shows a dot blot analysis of 8.31 expression. Messenger RNA (2 µg) was used in the dot blot to examine the expression of 8.31 in various tissues of hematopoietic origin as well as fetal tissues. Results of the hybridization using full-length 8.31 cDNA as probe are shown. Adult cells (top and middle rows) are (left to right, top to bottom) small intestine, spleen, thymus, peripheral leukocyte, lymph node, bone marrow, trachea and placenta. Fetal cells (bottom row) are (left to right) kidney, liver, spleen thymus and lung.

Dot blot analysis was performed to examine the expression of 8.31 in hematopoietic tissues. Expression of 8.31 was detected in all hematopoietic tissues examined; however, 8.31 was predominantly expressed in the thymus and the bone marrow. Lower transcript expression of 8.31 was detected in the spleen and lymph node. Only a barely detectable level of its expression was observed in the peripheral leukocytes (FIG. 4).

Figure 5:
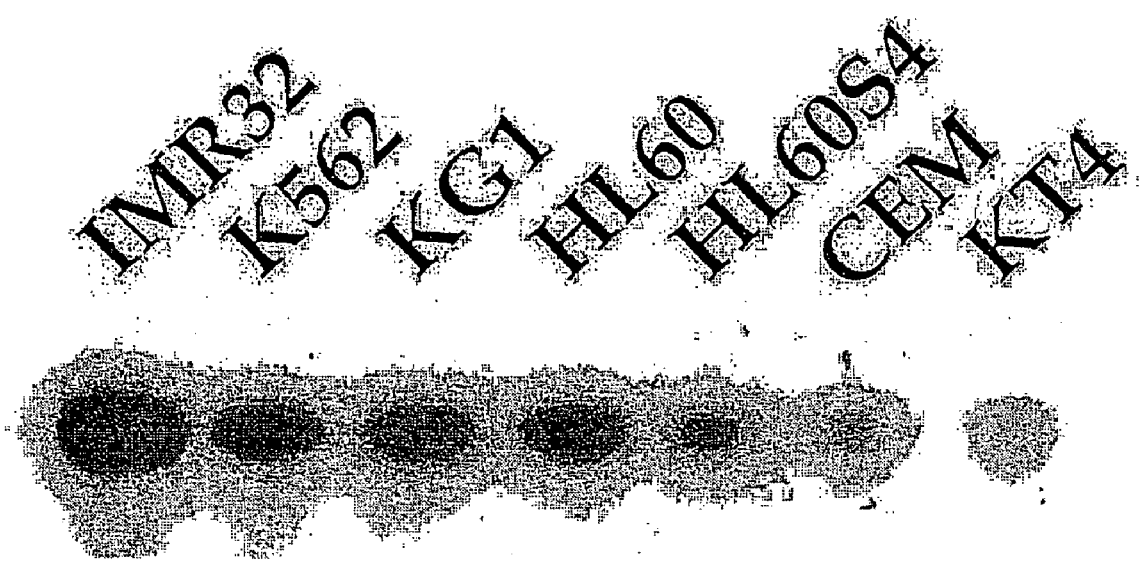
FIG. 5 shows RT-PCR analysis of the 8.31 expression in human cell lines. Total RNA (2 µg) obtained from neuronal precursor cell lines IMR32 and leukaemia cells was reverse transcribed and amplified by specific primers for 8.31. KT4 represents treatment of KG1 cells with all-trans RA for 4 days. Hybridization was performed to confirm the identity of the amplified products.

Expression of 8.31 in Different Human Cell Lines:

Owing to the high expression of 8.31 detected in the hematopoietic tissues, we have examined its expression in several leukaemia cell lines to obtain clues on its roles in hematopoietic systems. RT PCR analysis was performed using total RNA prepared from K562, KG1, HL-60, HL-60S4, and CEM, cell lines each corresponding to a different type of leukaemia (FIG. 5). Transcript expression of 8.31 was observed in all hematopoietic cell lines tested. Its expression was also observed in a human neuroblastoma cell line, IMR32 cells.

Figure 6:
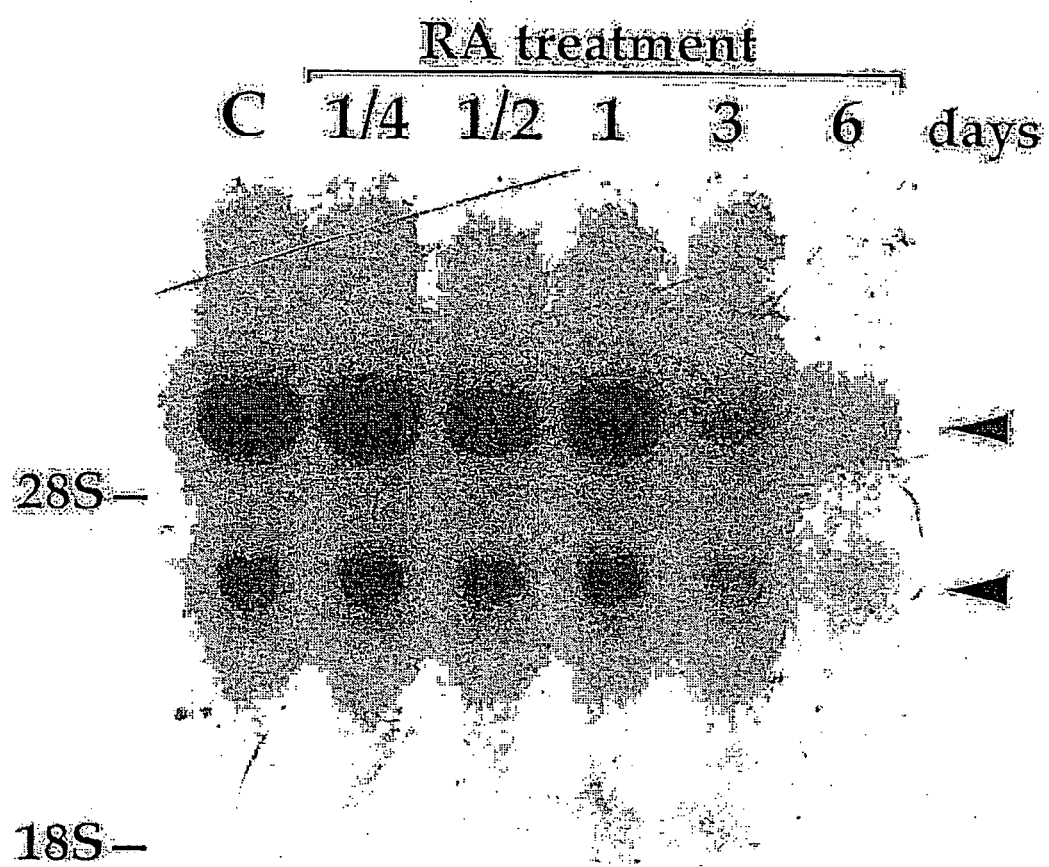
FIG. 6 shows expression of 8.31 in RA-treated HL-60 cells. Total RNA (15 µg) from HL-60 cells treated with 0 to 6 days was used for Northern blot analysis using full-length 8.31 cDNA probe. Ribosomal RNA bands are indicated on the left.

Expression of 8.31 was Down-Regulated in RA-treated HL-60 and KG1 Cells:

HL-60 cells were differentiated with 1 µM all-trans RA and the expression of 8.31 was examined by Northern blot analysis. Two transcripts (~5.5 kb and ~3.5 kb) were detected in undifferentiated HL-60 cells (FIG. 6). When HL-60 cells were treated with RA for 3 days, its expression was significantly down-regulated (FIG. 6). At day 6 of RA treatment, the expression of 8.31 was diminished.

The expression of 8.31 was also down-regulated when KG1 cells were treated with 1 µM all-trans RA, as demonstrated by the RT-PCR analysis (FIG. 5).

Figure 7:
FIG. 7 shows chromosomal localization of the gene 8.31 by FISH. Gene 8.31 was labelled and is shown marked "A", and the specific marker for the heterochromatin of chromosome 1 was labeled and so is shown marked "B"

Chromosomal Localization of Clone 8.31 by Fluorescence In Situ Hybridization:

DNA from a genomic clone of 8.31 was labeled with digoxigenin dUTP by nick translation. Labeled probe was combined with sheared human DNA and hybridized to normal metaphase chromosomes derived from PHA stimulated peripheral blood lymphocytes. The initial experiment resulted in specific labelling of the long arm of a group A chromosome which was believed to be chromosome 1 on the basis of size, morphology, and banding pattern. A second experiment was conducted in which a biotin-labelled probe specific for the heterochromactic region of chromosome 1 was co-hybridized with the genomic clone of 8.31. This experiment resulted in a specific labeling of the heterochromatin in red (marked "B" in FIG. 7) and the long arm in green (marked "A" in FIG. 7) of the chromosome 1. Measurements of 10 specifically labeled chromosomes 1 demonstrated that the genomic clone of 8.31 is located at a position which is 62% of the distance from the heterochromatic-euchromatic boundary to the telomere of chromosome arm 1q, an area which corresponds to band 1q32.1-32.2 (FIG. 7). A total of 80 metaphase cells were analyzed with 76 exhibiting specific labelling.

Type II Ushers syndrome (classical retinitis pigmentosa combined with congenital pedial deafness, and normal vestibular function) has been mapped to the chromosomal region containing the gene of the present invention (Kimberling et al., 1990, Genomics, 2: 245-249); Lewis et al., 1990, Genomics, 2: 250-256) and it appears that the gene of the present invention, together with its expression product, may be useful in the treatment of Ushers syndrome. For example, the lack of function resulting from mutations in the diseased gene may be complemented by the gene and/or expression products of the present invention.

Functional Roles of 8.31:

The expression profile observed for 8.31 suggests a potential role in tissues of hematopoietic origin. Recently, placental blood has been used as a rich source of hematopoietic stem cells for transplantation. Taken together with the high expression of 8.31 in the testis and the undifferentiated NT2 cells, the expression of 8.31 in placenta revealed a strong association of the gene to the identity of the stem cells. Hence it appears that the gene product of 8.31 is important in maintaining the stem cell identity of the progenitor cells, as well as in the early differentiation of the progenitor cells.

The expression of 8.31 is also strongly associated with the early embryonic development. This is exemplified by the high expression of 8.31 in fetal tissues such as brain, lung, liver and kidney, but not in same adult tissues. Together with its restrictive expression pattern in the adult tissues, it appears that the gene product of 8.31 is not only important in the embryogenesis, but is also participates in the functioning of these adult tissues. Different 8.31 isoforms exist, the expression of which can be regulated during the development (FIG. 3).

The predominant expression of 8.31 in the thymus and the bone marrow, but low expression in other lymphoid tissues revealed its restrictive functions in the T-cell lineage of the immune system.

Involvement of 8.31 in the Differentiation of Cancer Cells:

Northern blot analysis demonstrated the down-regulation of 8.31 expression with the treatment of all-trans RA. HL-60 is an acute promyelocytic leukaemia cell line. The growth rate was sharply decreased by treatment with RA. It appears that the expression of 8.31 is strongly associated with the differentiation of other cancer cell lines, including the embryonal carcinoma cells and the neuroblastoma cells. Hence 8.31 may serve as a diagnostic marker for different cancer types.

8.31 as a Candidate Gene for Genetic Diseases:

The gene encoding 8.31 was localized to the chromosome 1q32.1 32.2 Chromosome 1q 32 locus has been mapped to several genetic diseases including the complement system malfunctioning, as well as the Usher disease, which is related to hearing. Moreover the Alzheimer's disease is also mapped to the region 1q32, although the exact position remains to be elucidated.

Unless stated otherwise, all procedures were performed using standard protocols and following manufacturer's instructions where applicable. Standard protocols for various techniques including PCR, molecular cloning, manipulation and sequencing, the manufacture of antibodies, epitope mapping and mimotope design, cell culturing and phage display, are described in texts such as McPherson, M. J. et al. (1991, PCR: A practical approach, Oxford University Press, Oxford), Sambrook, J. et al. (1989, Molecular cloning: a laboratory manual, Cold Spring Harbour Laboratory, New York), Huynh and Davies (1985, "DNA Cloning Vol I-A Practical Approach", IRL Press, Oxford, Ed. D. M. Glover), Sanger, F. et al. (1977, PNAS USA 74(12): 5463-5467), Harlow, E. and Lane, D. ("Using Antibodies: A Laboratory Manual", Cold Spring Habour Laboratory Press, New York, 1998), Jung, G. and Beck-Sickinger, A. G. (1992, Angew. Chem. Int. Ed. Eng., 31: 367-486), Harris, M. A. and Rae, I. F. ("General Techniques of Cell Culture", 1997, Cambridge University Press, ISBN 0521 573645), "Phage Display of Peptides and Proteins: A Laboratory Manual" (Eds. Kay, B. K., Winter, J., and McCafferty, J., Academic Press Inc., 1996, ISBN 0-12-402380-0). Reagents and equipment useful in, amongst others, the methods detailed herein are available from the likes of Amersham, Boehringer Mannheim, Clontech, Genosys, Millipore, Novagen, Perkins Elmer, Pharmacia, Promega, Qiagen, Sigma and Stratagene.

We claim:

1. An isolated nucleic acid having the sequence of SEQ ID NO:1.

2. A recombinant DNA construct comprising operatively linked in sequence in the 5' to 3' direction:
   a) a promoter region that directs the transcription of a gene;
   b) a DNA coding sequence encoding an RNA sequence encoding an expression product having the sequence of SEQ ID NO:2; and
   c) a 3' non-translated region.

3. A recombinant DNA construct according to claim 2, wherein the DNA coding sequence has the sequence of SEQ ID NO:1.

4. A cell transformed or transfected with the recombinant DNA construct of claim 2.

* * * * *

UNITED STATES PATENT AND TRADEMARK OFFICE
CERTIFICATE OF CORRECTION

PATENT NO. : 7,276,595 B2 Page 1 of 1
APPLICATION NO. : 10/726160
DATED : October 2, 2007
INVENTOR(S) : Nancy Y. Ip and William M. W. Cheung It is certified that error appears in the above-identified patent and that said Letters Patent is hereby corrected as shown below:

On the Title Page, Item (75)
Inventor William M. W. Cheung address reads "Sunshine" should read
--Sunshine City--

Item (73)
Assignee reads "Hong Kong University of Science & Technology, Inc." should read
--Hong Kong University of Science and Technology--

Signed and Sealed this

Sixth Day of May, 2008

JON W. DUDAS
*Director of the United States Patent and Trademark Office*

UNITED STATES PATENT AND TRADEMARK OFFICE
CERTIFICATE OF CORRECTION

PATENT NO.         : 7,276,595 B2
APPLICATION NO. : 10/726160
DATED                 : October 2, 2007
INVENTOR(S)       : Nancy Y. Ip and William M. W. Cheung It is certified that error appears in the above-identified patent and that said Letters Patent is hereby corrected as shown below:

On the Title Page, Item (75)
Inventor William M. W. Cheung address reads "Sunshine" should read
--Sunshine City--

Item (73)
Assignee reads "Hong Kong University of Science & Technology, Inc." should read
--The Hong Kong University of Science and Technology--

This certificate supersedes the Certificate of Correction issued May 6, 2008.

Signed and Sealed this

Twenty-second Day of July, 2008

JON W. DUDAS
*Director of the United States Patent and Trademark Office*

SEQUENCE LISTING

<160> NUMBER OF SEQ ID NOS: 5

<210> SEQ ID NO 1
<211> LENGTH: 2831
<212> TYPE: DNA
<213> ORGANISM: Homo sapiens
<220> FEATURE:
<221> NAME/KEY: CDS
<222> LOCATION: (124)..(2313)

<400> SEQUENCE: 1

```
ggcacgagcg ggagttggag gcgataacga tttgtgttgt gagaggcgca acgtgcgatt      60
tctgctgaac ttggaggcat ttctacgact tttctctcag ctgaggcttt tcctccgacc     120 ctg atg ctc ttc aat tcg gtg ctc cgc cag ccc cag ctt ggc gtc ctg      168
    Met Leu Phe Asn Ser Val Leu Arg Gln Pro Gln Leu Gly Val Leu
    1               5                  10                  15 aga aat gga tgg tct tca caa tac cct ctt caa tcc ctt ctg act ggt      216
Arg Asn Gly Trp Ser Ser Gln Tyr Pro Leu Gln Ser Leu Leu Thr Gly
                20                  25                  30 tat cag tgc agt ggt aat gat gaa cac act tct tat gga gaa aca gga      264
Tyr Gln Cys Ser Gly Asn Asp Glu His Thr Ser Tyr Gly Glu Thr Gly
            35                  40                  45 gtc cca gtt cct cct ttt gga tgt acc ttc tct tct gct ccc aat atg      312
Val Pro Val Pro Pro Phe Gly Cys Thr Phe Ser Ser Ala Pro Asn Met
        50                  55                  60 gaa cat gta cta gca gtt gcc aat gaa gaa ggc ttt gtt cga ttg tat      360
Glu His Val Leu Ala Val Ala Asn Glu Glu Gly Phe Val Arg Leu Tyr
    65                  70                  75 aac aca gaa tca caa agt ttc aga aag aag tgc ttc aaa gaa tgg atg      408
Asn Thr Glu Ser Gln Ser Phe Arg Lys Lys Cys Phe Lys Glu Trp Met
80                  85                  90                  95 gct cac tgg aat gcc gtc ttt gac ctg gcc tgg gtt cct ggt gaa ctt      456
Ala His Trp Asn Ala Val Phe Asp Leu Ala Trp Val Pro Gly Glu Leu
                100                 105                 110 aaa ctt gtt aca gca gca ggt gat caa aca gcc aaa ttt tgg gac gta      504
Lys Leu Val Thr Ala Ala Gly Asp Gln Thr Ala Lys Phe Trp Asp Val
            115                 120                 125 aaa gct ggt gag ctg att gga aca tgc aaa ggt cat caa tgc agc ctc      552
Lys Ala Gly Glu Leu Ile Gly Thr Cys Lys Gly His Gln Cys Ser Leu
        130                 135                 140 aag tca gtt gcc ttt tct aag ttt gag aaa gct gta ttc tgt acg ggt      600
Lys Ser Val Ala Phe Ser Lys Phe Glu Lys Ala Val Phe Cys Thr Gly
    145                 150                 155 gga aga gat ggc aac att atg gtc tgg gat acc agg tgc aac aaa aaa      648
Gly Arg Asp Gly Asn Ile Met Val Trp Asp Thr Arg Cys Asn Lys Lys
160                 165                 170                 175 gat ggg ttt tat agg caa gtg aat caa atc agt gga gct cac aat acc      696
Asp Gly Phe Tyr Arg Gln Val Asn Gln Ile Ser Gly Ala His Asn Thr
                180                 185                 190 tca gac aag caa acc cct tca aaa ccc aag aag aaa cag aat tca aaa      744
Ser Asp Lys Gln Thr Pro Ser Lys Pro Lys Lys Lys Gln Asn Ser Lys
            195                 200                 205 gga ctt gct cct tct gtg gat ttc cag caa agt gtt act gtg gtc ctc      792
Gly Leu Ala Pro Ser Val Asp Phe Gln Gln Ser Val Thr Val Val Leu
        210                 215                 220 ttt caa gac gag aat acc tta gtc tca gca gga gct gtg gat ggg ata      840
Phe Gln Asp Glu Asn Thr Leu Val Ser Ala Gly Ala Val Asp Gly Ile
    225                 230                 235
```

-continued

| | | |
|---|---|---|
| atc aaa gta tgg gat tta cgt aag aat tat act gct tat cga caa gaa<br>Ile Lys Val Trp Asp Leu Arg Lys Asn Tyr Thr Ala Tyr Arg Gln Glu<br>240                        245                    250                      255 | 888 |
| ccc ata gca tcc aag tct ttc ctg tac cca ggt agc agc act cga aaa<br>Pro Ile Ala Ser Lys Ser Phe Leu Tyr Pro Gly Ser Ser Thr Arg Lys<br>                    260                    265                    270 | 936 |
| ctt gga tat tca agt ctg att ttg gat tcc act ggc tct act tta ttt<br>Leu Gly Tyr Ser Ser Leu Ile Leu Asp Ser Thr Gly Ser Thr Leu Phe<br>            275                    280                    285 | 984 |
| gct aat tgc aca gac gat aac atc tac atg ttt aat atg act ggg ttg<br>Ala Asn Cys Thr Asp Asp Asn Ile Tyr Met Phe Asn Met Thr Gly Leu<br>         290                    295                    300 | 1032 |
| aag act tct cca gtg gct att ttc aat gga cac cag aac tct acc ttt<br>Lys Thr Ser Pro Val Ala Ile Phe Asn Gly His Gln Asn Ser Thr Phe<br>305                        310                    315 | 1080 |
| tat gta aaa tcc agc ctt agt cca gat gac cag ttt tta gtc agt ggc<br>Tyr Val Lys Ser Ser Leu Ser Pro Asp Asp Gln Phe Leu Val Ser Gly<br>320                        325                    330                    335 | 1128 |
| tca agt gat gaa gct gcc tac ata tgg aag gtc tcc aca ccc tgg caa<br>Ser Ser Asp Glu Ala Ala Tyr Ile Trp Lys Val Ser Thr Pro Trp Gln<br>                    340                    345                    350 | 1176 |
| cct cct act gtg ctc ctg ggt cat tct caa gag gtc acg tct gtg tgc<br>Pro Pro Thr Val Leu Leu Gly His Ser Gln Glu Val Thr Ser Val Cys<br>            355                    360                    365 | 1224 |
| tgg tgt cca tct gac ttc aca aag att gct acc tgt tct gat gac aat<br>Trp Cys Pro Ser Asp Phe Thr Lys Ile Ala Thr Cys Ser Asp Asp Asn<br>         370                    375                    380 | 1272 |
| aca cta aaa atc tgg cgc ttg aat aga ggc tta gag gag aaa cca gga<br>Thr Leu Lys Ile Trp Arg Leu Asn Arg Gly Leu Glu Glu Lys Pro Gly<br>385                        390                    395 | 1320 |
| ggt gat aaa ctt tcc acg gtg ggt tgg gcc tct cag aag aaa aaa gag<br>Gly Asp Lys Leu Ser Thr Val Gly Trp Ala Ser Gln Lys Lys Lys Glu<br>400                        405                    410                    415 | 1368 |
| tca aga cct ggc cta gta aca gta acg agt agc cag agt act cct gcc<br>Ser Arg Pro Gly Leu Val Thr Val Thr Ser Ser Gln Ser Thr Pro Ala<br>                    420                    425                    430 | 1416 |
| aaa gcc ccc agg gta aag tgc aat cca tcc aat tct tcc ccg tca tcc<br>Lys Ala Pro Arg Val Lys Cys Asn Pro Ser Asn Ser Ser Pro Ser Ser<br>            435                    440                    445 | 1464 |
| gca gct tgt gcc cca agc tgt gct gga gac ctc cct ctt cct tca aat<br>Ala Ala Cys Ala Pro Ser Cys Ala Gly Asp Leu Pro Leu Pro Ser Asn<br>         450                    455                    460 | 1512 |
| act cct acg ttc tct att aaa acc tct cct gcc aag gcc cgg tct ccc<br>Thr Pro Thr Phe Ser Ile Lys Thr Ser Pro Ala Lys Ala Arg Ser Pro<br>465                        470                    475 | 1560 |
| atc aac aga aga ggc tct gtc tcc tcc gtc tct ccc aag cca cct tca<br>Ile Asn Arg Arg Gly Ser Val Ser Ser Val Ser Pro Lys Pro Pro Ser<br>480                        485                    490                    495 | 1608 |
| tct ttc aag atg tcg att aga aac tgg gtg acc cga aca cct tcc tca<br>Ser Phe Lys Met Ser Ile Arg Asn Trp Val Thr Arg Thr Pro Ser Ser<br>                    500                    505                    510 | 1656 |
| tca cca ccc atc act cca cct gct tcg gag acc aag atc atg tct ccg<br>Ser Pro Pro Ile Thr Pro Pro Ala Ser Glu Thr Lys Ile Met Ser Pro<br>            515                    520                    525 | 1704 |
| aga aaa gcc ctt att cct gtg agc cag aag tca tcc caa gca gag gct<br>Arg Lys Ala Leu Ile Pro Val Ser Gln Lys Ser Ser Gln Ala Glu Ala<br>         530                    535                    540 | 1752 |
| tgc tct gag tct aga aat aga gta aag agg agg cta gac tca agc tgt<br>Cys Ser Glu Ser Arg Asn Arg Val Lys Arg Arg Leu Asp Ser Ser Cys<br>545                        550                    555 | 1800 |

```
ctg gag agt gtg aaa caa aag tgt gtg aag agt tgt aac tgt gtg act      1848
Leu Glu Ser Val Lys Gln Lys Cys Val Lys Ser Cys Asn Cys Val Thr
560                 565                 570                 575 gag ctt gat ggc caa gtt gaa aat ctt cat ttg gat ctg tgc tgc ctt      1896
Glu Leu Asp Gly Gln Val Glu Asn Leu His Leu Asp Leu Cys Cys Leu
                580                 585                 590 gct ggt aac cag gaa gac ctt agt aag gac tct cta ggt cct acc aaa      1944
Ala Gly Asn Gln Glu Asp Leu Ser Lys Asp Ser Leu Gly Pro Thr Lys
            595                 600                 605 tca agc aaa att gaa gga gct ggt acc agt atc tca gag cct ccg tct      1992
Ser Ser Lys Ile Glu Gly Ala Gly Thr Ser Ile Ser Glu Pro Pro Ser
        610                 615                 620 cct atc agt ccg tat gct tca gaa agc tgt gga acg cta cct ctt cct      2040
Pro Ile Ser Pro Tyr Ala Ser Glu Ser Cys Gly Thr Leu Pro Leu Pro
    625                 630                 635 ttg aga cct tgt gga gaa ggg tct gaa atg gta ggc aaa gag aat agt      2088
Leu Arg Pro Cys Gly Glu Gly Ser Glu Met Val Gly Lys Glu Asn Ser
640                 645                 650                 655 tcc cca gag aat aaa aac tgg ttg ttg gcc atg gca gcc aaa cgg aag      2136
Ser Pro Glu Asn Lys Asn Trp Leu Leu Ala Met Ala Ala Lys Arg Lys
                660                 665                 670 gct gag aat cca tct cca cga agt ccg tca tcc cag aca ccc aat tcc      2184
Ala Glu Asn Pro Ser Pro Arg Ser Pro Ser Ser Gln Thr Pro Asn Ser
            675                 680                 685 agg aga cag agc gga aag aca ttg cca agc ccg gtc acc atc acg ccc      2232
Arg Arg Gln Ser Gly Lys Thr Leu Pro Ser Pro Val Thr Ile Thr Pro
        690                 695                 700 agc tcc atg agg aaa atc tgc aca tac ttc cat aga aag tcc cag gag      2280
Ser Ser Met Arg Lys Ile Cys Thr Tyr Phe His Arg Lys Ser Gln Glu
    705                 710                 715 gac ttc tgt ggt cct gaa cac tca aca gaa tta tagattctaa tctgagtgag    2333
Asp Phe Cys Gly Pro Glu His Ser Thr Glu Leu
720                 725                 730 ttactgagct ttggtccact aaaacaagct gagctttggt ccactaaaac aagatgaaaa   2393
atacaagagt gactctataa ctctggtctt taagaaagct gccttttcat ttttagacaa   2453
aatcttttca acgctgaaat gtacctaatc tggttctact accataatgt atatgcagct   2513
tcccgaggat gaatgctgtg tttaaatttc ataaagtaaa tttgtcactc tagcattttg   2573
aatgaatagt cttcactttt taaattattc atcttctcta taataatgac atcccagttc   2633
atggaggcaa aaaacaagtt tcttgttatc ctgaaacttt ctatgctcag tggaaagtat   2693
ctgccagcca cagcatgagg cctgtgaagg ctgactgaga aatcctctgc tgaagacccc   2753
tggttctgtt ctgcctccaa catgtataat tttatttgaa atacataatc ttttcactat   2813
gaaaaaaaaa aaaaaaaa                                                  2831

<210> SEQ ID NO 2
<211> LENGTH: 730
<212> TYPE: PRT
<213> ORGANISM: Homo sapiens

<400> SEQUENCE: 2

Met Leu Phe Asn Ser Val Leu Arg Gln Pro Gln Leu Gly Val Leu Arg
1               5                   10                  15

Asn Gly Trp Ser Ser Gln Tyr Pro Leu Gln Ser Leu Leu Thr Gly Tyr
            20                  25                  30

Gln Cys Ser Gly Asn Asp Glu His Thr Ser Tyr Gly Glu Thr Gly Val
        35                  40                  45
```

-continued

```
Pro Val Pro Pro Phe Gly Cys Thr Phe Ser Ala Pro Asn Met Glu
 50                  55                  60
His Val Leu Ala Val Ala Asn Glu Glu Gly Phe Val Arg Leu Tyr Asn
 65                  70                  75                  80
Thr Glu Ser Gln Ser Phe Arg Lys Lys Cys Phe Lys Glu Trp Met Ala
                 85                  90                  95
His Trp Asn Ala Val Phe Asp Leu Ala Trp Val Pro Gly Glu Leu Lys
            100                 105                 110
Leu Val Thr Ala Ala Gly Asp Gln Thr Ala Lys Phe Trp Asp Val Lys
            115                 120                 125
Ala Gly Glu Leu Ile Gly Thr Cys Lys Gly His Gln Cys Ser Leu Lys
130                 135                 140
Ser Val Ala Phe Ser Lys Phe Glu Lys Ala Val Phe Cys Thr Gly Gly
145                 150                 155                 160
Arg Asp Gly Asn Ile Met Val Trp Asp Thr Arg Cys Asn Lys Lys Asp
                165                 170                 175
Gly Phe Tyr Arg Gln Val Asn Gln Ile Ser Gly Ala His Asn Thr Ser
            180                 185                 190
Asp Lys Gln Thr Pro Ser Lys Pro Lys Lys Gln Asn Ser Lys Gly
            195                 200                 205
Leu Ala Pro Ser Val Asp Phe Gln Gln Ser Val Thr Val Leu Phe
    210                 215                 220
Gln Asp Glu Asn Thr Leu Val Ser Ala Gly Ala Val Asp Gly Ile Ile
225                 230                 235                 240
Lys Val Trp Asp Leu Arg Lys Asn Tyr Thr Ala Tyr Arg Gln Glu Pro
                245                 250                 255
Ile Ala Ser Lys Ser Phe Leu Tyr Pro Gly Ser Ser Thr Arg Lys Leu
            260                 265                 270
Gly Tyr Ser Ser Leu Ile Leu Asp Ser Thr Gly Ser Thr Leu Phe Ala
            275                 280                 285
Asn Cys Thr Asp Asp Asn Ile Tyr Met Phe Asn Met Thr Gly Leu Lys
290                 295                 300
Thr Ser Pro Val Ala Ile Phe Asn Gly His Gln Asn Ser Thr Phe Tyr
305                 310                 315                 320
Val Lys Ser Ser Leu Ser Pro Asp Asp Gln Phe Leu Val Ser Gly Ser
                325                 330                 335
Ser Asp Glu Ala Ala Tyr Ile Trp Lys Val Ser Thr Pro Trp Gln Pro
            340                 345                 350
Pro Thr Val Leu Leu Gly His Ser Gln Glu Val Thr Ser Val Cys Trp
            355                 360                 365
Cys Pro Ser Asp Phe Thr Lys Ile Ala Thr Cys Ser Asp Asp Asn Thr
370                 375                 380
Leu Lys Ile Trp Arg Leu Asn Arg Gly Leu Glu Glu Lys Pro Gly Gly
385                 390                 395                 400
Asp Lys Leu Ser Thr Val Gly Trp Ala Ser Gln Lys Lys Glu Ser
                405                 410                 415
Arg Pro Gly Leu Val Thr Val Thr Ser Ser Gln Ser Thr Pro Ala Lys
            420                 425                 430
Ala Pro Arg Val Lys Cys Asn Pro Ser Asn Ser Ser Pro Ser Ser Ala
            435                 440                 445
Ala Cys Ala Pro Ser Cys Ala Gly Asp Leu Pro Leu Pro Ser Asn Thr
450                 455                 460
```

```
Pro Thr Phe Ser Ile Lys Thr Ser Pro Ala Lys Ala Arg Ser Pro Ile
465                 470                 475                 480

Asn Arg Arg Gly Ser Val Ser Ser Val Ser Pro Lys Pro Pro Ser Ser
                485                 490                 495

Phe Lys Met Ser Ile Arg Asn Trp Val Thr Arg Thr Pro Ser Ser Ser
            500                 505                 510

Pro Pro Ile Thr Pro Pro Ala Ser Glu Thr Lys Ile Met Ser Pro Arg
        515                 520                 525

Lys Ala Leu Ile Pro Val Ser Gln Lys Ser Ser Gln Ala Glu Ala Cys
    530                 535                 540

Ser Glu Ser Arg Asn Arg Val Lys Arg Arg Leu Asp Ser Ser Cys Leu
545                 550                 555                 560

Glu Ser Val Lys Gln Lys Cys Val Lys Ser Cys Asn Cys Val Thr Glu
                565                 570                 575

Leu Asp Gly Gln Val Glu Asn Leu His Leu Asp Leu Cys Cys Leu Ala
            580                 585                 590

Gly Asn Gln Glu Asp Leu Ser Lys Asp Ser Leu Gly Pro Thr Lys Ser
        595                 600                 605

Ser Lys Ile Glu Gly Ala Gly Thr Ser Ile Ser Glu Pro Pro Ser Pro
    610                 615                 620

Ile Ser Pro Tyr Ala Ser Glu Ser Cys Gly Thr Leu Pro Leu Pro Leu
625                 630                 635                 640

Arg Pro Cys Gly Glu Gly Ser Glu Met Val Gly Lys Glu Asn Ser Ser
                645                 650                 655

Pro Glu Asn Lys Asn Trp Leu Leu Ala Met Ala Ala Lys Arg Lys Ala
            660                 665                 670

Glu Asn Pro Ser Pro Arg Ser Pro Ser Ser Gln Thr Pro Asn Ser Arg
        675                 680                 685

Arg Gln Ser Gly Lys Thr Leu Pro Ser Pro Val Thr Ile Thr Pro Ser
    690                 695                 700

Ser Met Arg Lys Ile Cys Thr Tyr Phe His Arg Lys Ser Gln Glu Asp
705                 710                 715                 720

Phe Cys Gly Pro Glu His Ser Thr Glu Leu
                725                 730

<210> SEQ ID NO 3
<211> LENGTH: 83
<212> TYPE: DNA
<213> ORGANISM: Homo sapiens

<400> SEQUENCE: 3
tttgagaaag ctgtattctg tacgggtgga agagatggca acattatggt ctgggatacc    60
aggtgcaaca aaaaagatgg gtt                                            83

<210> SEQ ID NO 4
<211> LENGTH: 25
<212> TYPE: PRT
<213> ORGANISM: Homo Sapiens

<400> SEQUENCE: 4

Ala Lys Arg Lys Ala Glu Asn Pro Ser Pro Arg Ser Pro Ser Ser Gln
1               5                   10                  15

Thr Pro Asn Ser Arg Arg Gln Ser Gly
            20                  25

<210> SEQ ID NO 5
```

```
-continued

<211> LENGTH: 25
<212> TYPE: PRT
<213> ORGANISM: Homo sapiens

<400> SEQUENCE: 5

Thr Gly Tyr Gln Cys Ser Gly Asn Asp Glu His Thr Ser Tyr Gly Glu
1               5                   10                  15

Thr Gly Val Pro Val Pro Pro Phe Gly
            20                  25
```